(12) United States Patent
Buckland et al.

(10) Patent No.: US 8,120,779 B2
(45) Date of Patent: Feb. 21, 2012

(54) OPTICAL COHERENCE IMAGING SYSTEMS HAVING A MECHANISM FOR SHIFTING FOCUS AND SCANNING MODALITY

(75) Inventors: Eric L. Buckland, Hickory, NC (US);
Joseph A. Izatt, Raleigh, NC (US);
Seungbum Woo, Bridgewater, NJ (US);
Michael E. Sullivan, Raleigh, NC (US)

(73) Assignee: Bioptigen, Inc., Durham, NC (US)

( * ) Notice: Subject to any disclaimer, the term of this patent is extended or adjusted under 35 U.S.C. 154(b) by 0 days.

(21) Appl. No.: 12/868,913

(22) Filed: Aug. 26, 2010

(65) Prior Publication Data
US 2010/0315592 A1    Dec. 16, 2010

Related U.S. Application Data

(63) Continuation of application No. 11/930,865, filed on Oct. 31, 2007, now Pat. No. 7,830,525.

(60) Provisional application No. 60/855,821, filed on Nov. 1, 2006.

(51) Int. Cl.
*G02C 9/02* (2006.01)
(52) U.S. Cl. .......................... 356/479; 356/477
(58) Field of Classification Search .............. 351/221, 351/205, 200; 356/479, 477, 497
See application file for complete search history.

(56) References Cited

U.S. PATENT DOCUMENTS

| | | | |
|---|---|---|---|
| 5,321,501 A | 6/1994 | Swanson et al. | |
| 5,491,524 A | 2/1996 | Hellmuth et al. | |
| 6,095,648 A | 8/2000 | Birngruber et al. | |
| 6,741,359 B2 | 5/2004 | Wei et al. | |
| 7,236,251 B2 * | 6/2007 | Takaoka | 356/497 |
| 7,301,644 B2 | 11/2007 | Knighton et al. | |
| 7,830,525 B2 | 11/2010 | Buckland et al. | |
| 2004/0066489 A1 | 4/2004 | Benedikt et al. | |
| 2007/0291277 A1 | 12/2007 | Everett et al. | |

FOREIGN PATENT DOCUMENTS
EP   1 602 320 A1   12/2005
WO   WO 01/95791 A1  12/2001

OTHER PUBLICATIONS

Swanson et al., "In vivo retinal imaging by optical coherence tomography", Optics Letters, vol. 18:21, pp. 1864-1866 (Nov. 1, 1993).
Radhakrishnan et al., "Real-Time Optical Coherence Tomography of the Anterior Segment at 1310 nm", Arch. Ophthalmol., vol. 119, pp. 1179-1185 (Aug. 2001).
J.A. Izatt, PhD. et al., "Micrometer-Scale Resolution Imaging of the Anterior Eye in Vivo With Optical Coherence Tomography", Arch. Ophthalmol., vol. 112, pp. 1584-1589 (Dec. 1994).
International Search Report, PCT/US2007/023094, Mar. 28, 2008.
Kalev-Landoy et al., "Optical coherence tomography in anterior segment imaging," ACTA Ophthalmologica Scandinavic 2007, pp. 427-430.
Leung et al., "Visualization of Anterior Chamber Angle Dynamics Using Optical Coherence Tomography," American Academy of Ophthalmology, 2005, pp. 980-984.

* cited by examiner

*Primary Examiner* — Hung Dang
(74) *Attorney, Agent, or Firm* — Myers Bigel Sibley & Sajovec

(57) ABSTRACT

Some embodiments of the present invention provide adapters for use in posterior imaging systems. The adapters include lens set configured to adapt the posterior imaging system to operate as an anterior imaging system. Related optical coherence tomography systems and anterior imaging systems are also provided herein.

35 Claims, 4 Drawing Sheets

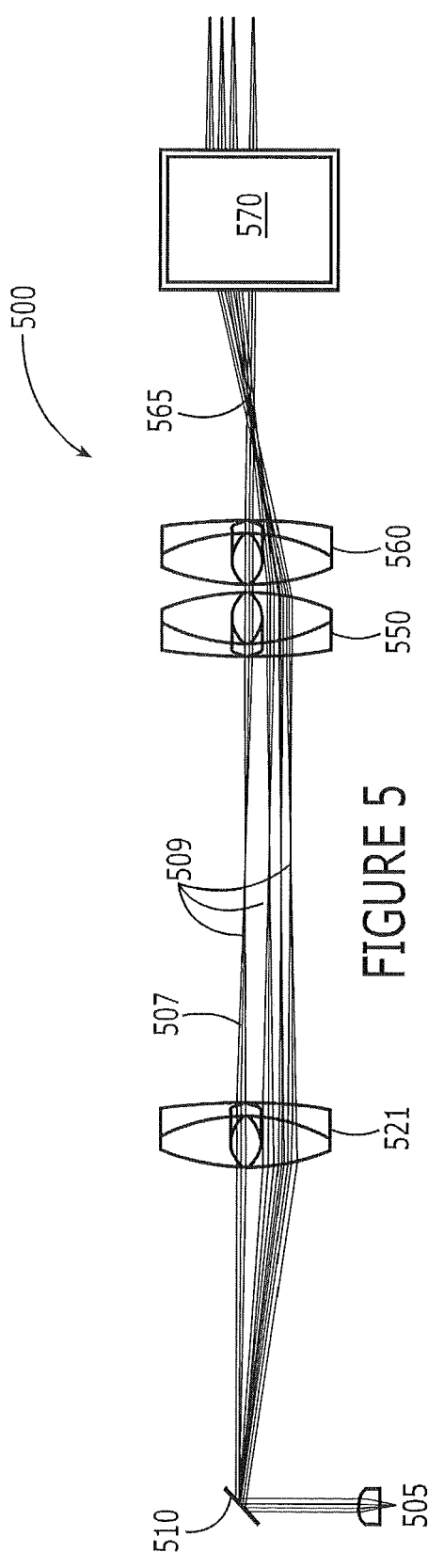
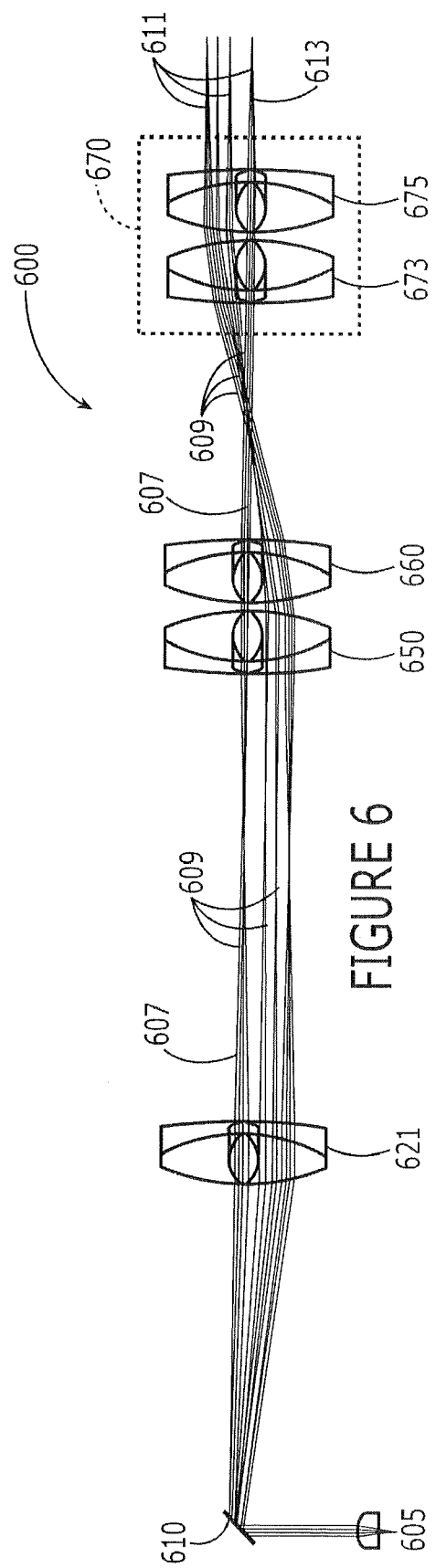

OPTICAL COHERENCE IMAGING SYSTEMS HAVING A MECHANISM FOR SHIFTING FOCUS AND SCANNING MODALITY

CLAIM FOR PRIORITY

The present application is a continuation of U.S. patent application Ser. No. 11/930,865, filed Oct. 31, 2007, now U.S. Pat. No. 7,830,525 which claims priority from U.S. Provisional Application No. 60/855,821, filed Nov. 1, 2006, the disclosures of which are hereby incorporated herein by reference as if set forth in their entirety.

FIELD OF THE INVENTION

The present invention relates to imaging and, more particularly, to optical coherence tomography (OCT) and related systems and devices.

BACKGROUND OF THE INVENTION

A variety of approaches to imaging using optical coherence tomography (OCT) are known. Such systems may be characterized as Fourier domain OCT (FD-OCT) and time domain OCT (TD-OCT). FD-OCT generally includes swept source (SS) and spectral domain (SD), where SD systems generally use spectrometers rather than a swept source. TD systems generally rely on movement of a mirror or reference source over time to control imaging depth. In contrast, for FD-OCT, the imaging depth may be determined from a Fourier transform of the acquired spectrum, rather than by the range of a physically scanned mirror. Specifically, in FD-OCT, the number of samples of the spectrum may be used to control the imaging depth, with a greater number of samples of spectrum providing a deeper imaging capability.

OCT imaging systems are well known for use in ophthalmic imaging, and have been applied commercially for posterior imaging of the retina (hereinafter "posterior imaging systems"), and for anterior imaging of the cornea and the anterior chamber (hereinafter "anterior imaging systems"). Posterior imaging systems for imaging the posterior region of the eye and anterior imaging systems for imaging anterior segments of the eye may require different penetration depths, imaging depths, focal positions, and/or scanning optics. Generally, posterior imaging systems developed for high quality posterior imaging applications have not been applicable to high quality anterior applications. Conversely, anterior imaging systems developed for high quality anterior imaging applications have not been applicable to high quality posterior applications In particular, posterior imaging systems developed for posterior imaging typically utilize the cornea and the lens of the eye as effective components of the integrated imaging system. The imaging system including these anterior components of the eye is designed to focus the scanning beam on the retina, approximately 24 mm from the cornea surface. Additionally, the scanned beam is designed to angularly pivot around a point centered in the neighborhood of the iris and the lens, appropriate for scanning the curved retina at the rear of the posterior segment.

A sample arm of a conventional posterior imaging system will now be discussed with respect to FIG. 1. As illustrated therein, the posterior imaging system 100 includes a collimation optic 105, a scanning optic 110, a scan lens 121, an objective lens set 150/160 and a human eye (sample) 125. As illustrated, the human eye 125 includes an anterior segment 130, a posterior segment 135 and posterior pole 145. The collimation optic 105 is configured to collimate the light diverging from a fiber optic output. The scanning optic 110 may be, for example, a mirror mounted on a galvonometer, and may be configured to scan a beam over the scan lens 121. The scan lens 121 may be configured to parallelize the light coming off the scanning optic 110. In particular, the ray bundles 109 coming off the scanning optic 110 are diverging, but the rays 107 within the ray bundles 109 are collimated. After passing through the scan lens 121, the ray bundles 109 are made parallel, and the rays within each bundle are focused to a point between the scan lens and objective lens, thus they are diverging again when reaching the objective lens set. The objective lens set 150/160 is configured to collimate the rays 107 within the ray bundles 109, which are made to converge through the iris of the human eye 125 as a pivot point. The cornea and lens of the human eye serve to focus the rays within each bundle onto a separate point on the retina, thus imaging the intermediate focus between the scan lens and objective lens set onto the retina. In other words, posterior imaging systems 100 are designed to use the sample (human eye 125) as a component of the system 100.

Posterior imaging systems are discussed in detail in, for example, *In Vivo Retinal Imaging by Optical Coherence Tomography* by Swanson (Optics Letters, Vol. 18, No. 21 (Nov. 1, 1993)) and U.S. Pat. No. 5,321,501 to Swanson, the disclosures of which are hereby incorporated herein by reference as if set forth in their entirety.

Anterior imaging systems developed for anterior imaging generally treat the cornea as an object of the imaging system, rather than a component, and are generally designed to image the depth, width and structure of the anterior chamber from corneal surface to iris and lens. Such systems place the focus approximately 20 mm forward of the posterior imaging system, have an imaging depth of 6.0 to 10.0 mm, in contrast to the 0.5 to 2.0 mm typically required in posterior imaging systems, and are supported by telecentric or near-telecentric scanning geometries rather than the pivoting geometry used in the posterior imaging systems, for example, the posterior imaging system of FIG. 1.

A sample arm of a conventional anterior imaging system 200 will now be discussed with respect to FIG. 2. As illustrated therein, the anterior imaging system 200 includes a collimation optic 205, a scanning optic 210, a scan/objective lens 220 and a human eye as a sample 225. As illustrated, the human eye 225 includes an anterior segment 230, a posterior segment 235 and posterior pole 245. The collimation optic 205 is configured to collimate the light diverging from a fiber optic output. The scanning optic 210 may be, for example, a mirror mounted on a galvonometer, and may be configured to scan a beam over the scan/objective lens 220. The scan/objective lens 220 may be configured to parallelize and focus the light coming off the scanning optic 210. In particular, the ray bundles 209 coming off the scanning optic are diverging, but the rays 207 within the ray bundles 209 are collimated. After passing through the scan/objective lens 220, the ray bundles 209 are parallel, but the rays 207 within the ray bundles 209 are focusing on the object being imaged, here the anterior segment 230 of the human eye 225.

Anterior imaging systems are discussed in detail in, for example, *Micrometer-Scale Resolution Imaging of the Anterior Eye In Vivo with Optical Coherence Tomography* by Izatt et al. (Ophthalmology, Vol. 112, pp. 1584-1589 (December 1994)) and *Real-time Optical Coherence Tomography of the Anterior Segment at 1310 nm* by Radhakrishnan et al. (Ophthalmology, Vol. 119, pp. 1179-1185 (August 2001)), the disclosures of which are hereby incorporated herein by reference as if set forth in their entirety.

SUMMARY OF EMBODIMENTS OF THE INVENTION

Some embodiments of the present invention provide adapters for use in posterior imaging systems. The adapters include a lens set configured to adapt the posterior imaging system to operate as an anterior imaging system.

In further embodiments of the present invention, the lens set may include first and second lenses. The first and second lenses may have a focal length (F) of about 30.0 mm and a diameter (D) of about 25.4 mm. The first and second lenses may be Achromat doublet lenses.

In still further embodiments of the present invention, the lens set may include a multi-element lens. The multi-element lens may be configured to image a curved object onto a flat plane. The multi-element lens may be further configured so that a central ray of each of a plurality of ray bundles is normal to the curved object.

In some embodiments of the present invention, the multi-element lens may be configured to provide associated ray paths having substantially equal optical path lengths over an entire image.

Further embodiments of the present invention provide optical coherence tomography (OCT) systems including an adapter in a sample arm of the OCT system, the adapter being configured to adapt a posterior imaging system to operate as an anterior imaging system.

In still further embodiments of the present invention, the adapter may be configured to be received in the sample arm of the posterior imaging system to provide the anterior imaging system.

In some embodiments of the present invention, the adapter may include a lens set and the lens set may include first and second lenses. The first and second lenses may have a combined focal length (F) of about 30.0 mm and a diameter (D) of about 25.4 mm.

In further embodiments of the present invention, the adapter may include a lens set and the lens set may include a multi-element lens. The multi-element lens may be configured to image a curved object onto a flat plane. The multi-element lens may be further configured so that a central ray of each of a plurality of ray bundles is normal to the curved object.

In still further embodiments of the present invention, the multi-element lens may be configured to provide associated ray paths having substantially equal optical path lengths over an entire image.

In some embodiments of the present invention, the OCT system may further include a collimation optic, a scanning optic connected to the collimation optic, a scan lens connected to the scanning optic and an objective lens set between the scan lens and the adapter.

Further embodiments of the present invention provide an anterior imaging system including a posterior imaging system configured to receive an adapter configured to adapt the posterior imaging system to operate as an anterior imaging system, the adapter being positioned in the posterior imaging system In still further embodiments of the present invention, the adapter further includes a lens set and the lens set may include first and second lenses. The first and second lenses may have a focal length (F) of about 30.0 mm and a diameter (D) of about 25.4 mm.

In some embodiments of the present invention, the adapter may include a lens set and the lens set may include a multi-element lens configured to image a curved object onto a flat plane. The multi-element lens may be further configured so that a central ray of each of a plurality of ray bundles is normal to the curved object.

In further embodiments of the present invention, the multi-element lens may be configured to provide associated ray paths having substantially equal optical path lengths over an entire image.

Still further embodiments of the present invention provide a single imaging system configured to operate as a posterior imaging system or an anterior imaging system.

In some embodiments of the present invention, the single imaging system may include an adapter configured to adapt the imaging system to operate as either the posterior imaging system or as the anterior imaging system. The adapter may include a lens set configured to adapt the posterior imaging system to operate as an anterior imaging system.

BRIEF DESCRIPTION OF THE DRAWINGS

FIG. 5 is a block diagram illustrating a sample arm of an adaptable imaging system including an adapter according to some embodiments of the present invention.

FIG. 6 is a block diagram illustrating a sample arm of an adaptable imaging system including an adapter according to some embodiments of the present invention.

DETAILED DESCRIPTION OF THE INVENTION

Figure 1:
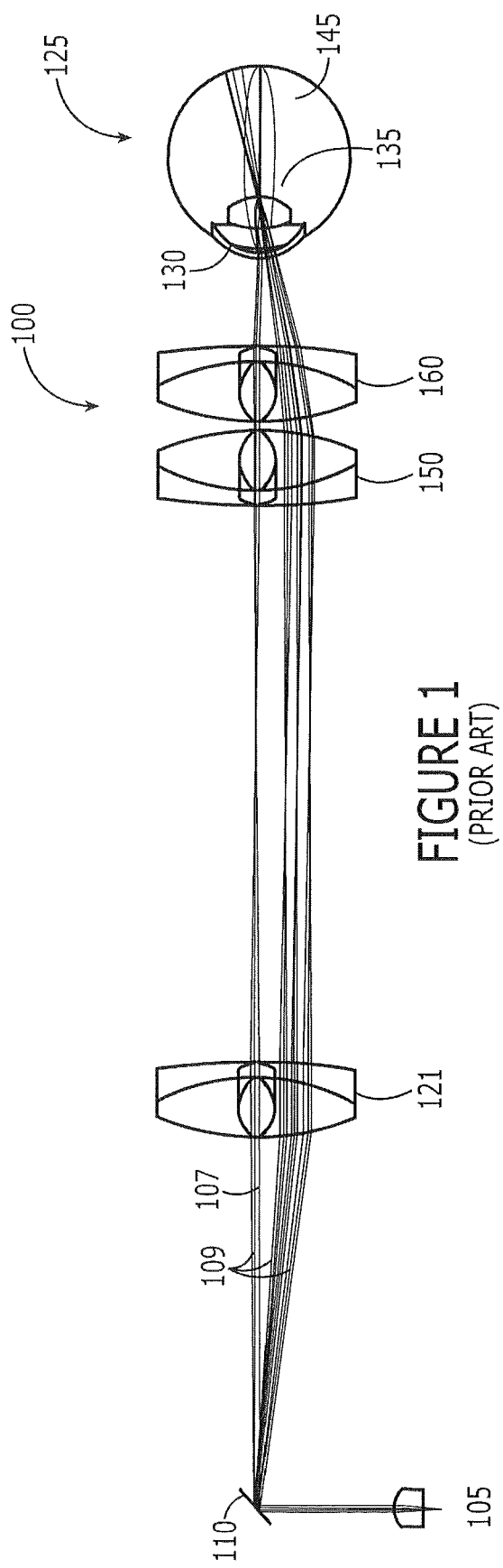
FIG. 1 is a diagram illustrating a sample arm of a conventional posterior imaging system.
Figure 2:
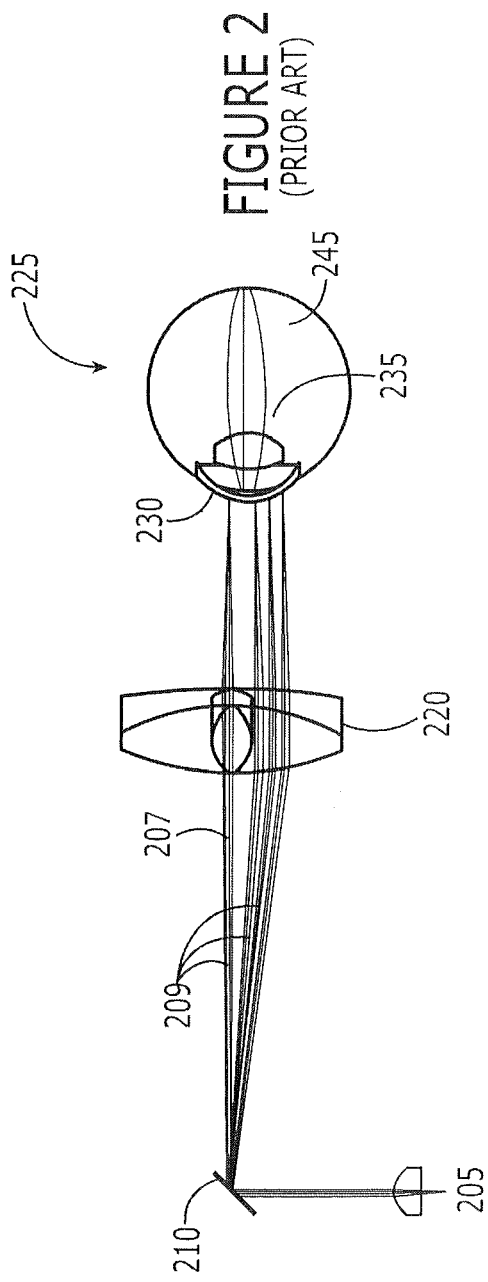
FIG. 2 is a diagram illustrating a sample arm of a conventional anterior imaging system.

Specific exemplary embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular exemplary embodiments illustrated in the accompanying drawings is not intended to be limiting of the invention. In the drawings, like numbers refer to like elements.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

As discussed in the background of the invention, "posterior imaging systems," i.e. systems used for posterior imaging of the retina, and "anterior imaging systems," systems for anterior imaging of the cornea and the anterior chamber are not typically interchangeable because they may require different penetration depths, imaging depths, focal positions, scanning optics and the like. However, in many cases, shallower imaging of the anterior chamber, for example, imaging the cornea only, imaging the sclera or conjunctiva, or imaging the anterior angle between sclera, cornea and iris, may be desirable. Such imaging may not require 6.0 mm of imaging depth, but still may require a shift of focal position and a telecentric scanning geometry relative to the retinal imaging.

Accordingly, some embodiments of the present invention provide OCT systems and adapters configured to operate a posterior imaging system as an anterior imaging system as will be discussed below with respect to FIGS. 3 through 7. It will be understood that although embodiments of the present invention only discuss modifying a posterior imaging system to operate as an anterior imaging system, embodiments of the present invention are not limited to this configuration. For example, anterior imaging systems may be modified to operate as posterior imaging systems without departing from the scope of the present invention.

Figure 3:
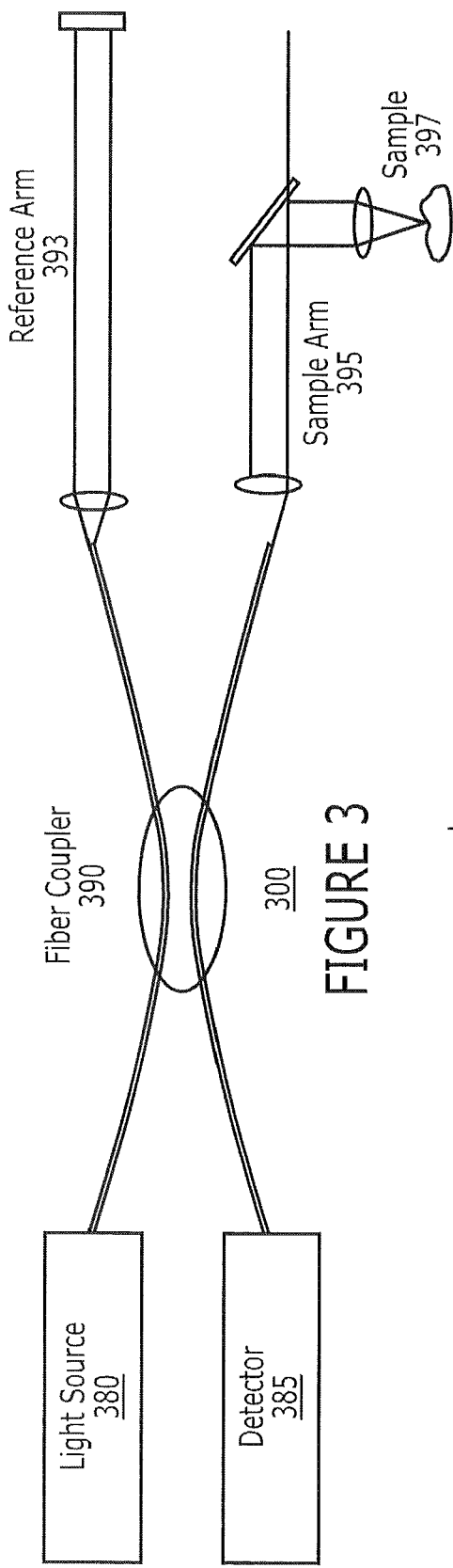
FIG. 3 is a block diagram of an OCT system that may include an adapter in the sample arm in accordance with some embodiments of the present invention.

Referring now to FIG. 3, a block diagram of an OCT system 300 that may include an adapter in the sample arm in accordance with embodiments of the present invention will be discussed. As illustrated in FIG. 3, the OCT system 300 may include a light source 380, a detector 385, a fiber coupler 390, a reference arm 393, a sample arm 395 and a sample 397. An adapter in accordance with some embodiments of the present invention may be included in the sample arm of the OCT system 300 as will be discussed further below with respect to FIGS. 5 through 7.

It will be understood that the OCT system 300 of FIG. 3 is provided herein for exemplary purposes only and that embodiments of the present invention are not limited to this configuration. Any OCT system may be used without departing from the scope of the present invention.

Figure 4:
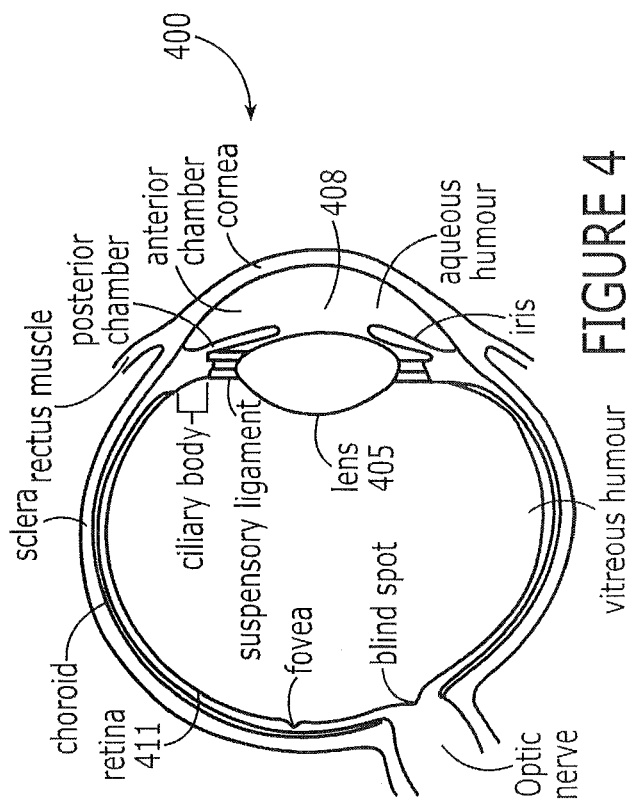
FIG. 4 is a diagram illustrating the human eye and the portions related to some embodiments of the present invention.

The sample of the OCT systems discussed in accordance with some embodiments of the present invention is the human eye. A diagram of the human eye is provided in FIG. 4. As illustrated in FIG. 4, the human eye 400 includes the portions illustrated therein. For purposes of the present application, the term "anterior segment" includes the lens and everything forward of the lens 405, the "posterior segment" includes the area behind the iris and lens 405 and the "posterior pole" includes the retina 411.

Some embodiments of the present invention may provide an adapter that allows the requirements of both the posterior and anterior imaging systems to be provided by one system. Referring first to FIG. 5, a block diagram illustrating a sample arm of an adaptable imaging system including an adapter according to some embodiments of the present invention will be discussed. Only the sample arm of the OCT system including the adapter in accordance with some embodiments of the present invention will be discussed herein as OCT systems in general are known to those having skill in the art.

As illustrated in FIG. 5, the adaptable system 500 according to some embodiments of the present invention includes a collimation optic 505, a scanning optic 510, a scan lens 521, an objective lens set 550/560 and an adapter 570 in accordance with some embodiments of the present invention. It will be understood that the term "lens" as used herein may include a single piece of glass, multiple pieces of glass or a system of lenses without departing from the scope of the present invention. Thus, any combination of the above that may act as one to image OCT may be used without departing from the scope of the present invention.

The collimation optic 505 is configured to collimate the light diverging from a fiber optic output onto the scanning optic 510. The scanning optic 510 may be, for example, a mirror mounted on a motor, and may be configured to scan a beam over the scan lens 521. Although the scanning optic 510 is discussed herein as being a mirror mounted on a galvonometer, embodiments of the present invention are not limited to this configuration. For example, the scanning optic 510 may be, for example, a galvonometer or fast scanning mirror (FSM). The scanning optic 510 may also be configured to scan in one or two dimensions without departing from the scope of the present invention.

The scan lens 521 may be configured to parallelize the light coming off the scanning optic 510. In particular, the ray bundles 509 coming off the scanning optic 510 are diverging, but the rays 507 within the ray bundles 509 are collimated. After passing through the scan lens 521, the ray bundles 509 are parallel, and the rays within each bundle are focusing to an intermediate focus position between the scan and objective lenses. The objective lens set 550/560 is configured to collimate the rays 507 within the ray bundles 509 and to focus the ray bundles through a pivot point coincident with the iris of the human eye (not shown); however, the ray bundles 509 are converging at point 565 as illustrated in FIG. 5. The first three lenses 521, 550 and 560 may have a focal length (F) of about 50.0 mm and diameter (D) of about 25.4 mm in accordance with some embodiments of the present invention.

The system 500 of FIG. 5 further includes an adapter 570 in accordance with some embodiments of the present invention. As discussed above, the adapter 570 is configured to allow a posterior imaging system to operate as an anterior imaging system. It will be understood that according to some embodiments of the present invention, the adapter 570 is configured to be placed into an existing posterior imaging system. After recalibration of the system 500 including the adapter 570, the system 500 will then operate as an anterior imaging system.

The adapter 570 may include any method of bending light, for example, refractive, reflective, defractive and the like without departing from the scope of the present invention as will be discussed further below with respect to FIGS. 6 and 7.

As is understood by those having skill in the art, the reference path length of an OCT system matches the path length of the sample arm. Thus, in some embodiments of the present invention, a reference path length of the interferometer may be changed to shift the path-length matching condition for operation of the optical coherence tomography interferometer. In certain embodiments of the present invention, the reference path length may be changed mechanically so that the reference path length matches the path length of the sample arm. In some embodiments of the present invention, multiple reference arms having different path lengths may be provided.

More detailed embodiments of the systems including adapters in accordance with some embodiments of the present invention will now be discussed with respect to FIGS. 6 and 7. Although embodiments of the present invention are discussed herein with respect to the sample of the OCT system being a human eye, embodiments of the present invention are not limited to this configuration.

Referring now to FIG. 6, an OCT system including adapter in accordance with some embodiments of the present invention will be discussed. Like reference numbers refer to like elements throughout the specification. Thus, the details with respect to the collimation optic 605, the scanning optic 610, the scan lens 621 and the objective lens set 650/660 are similar to those discussed above with respect to FIG. 5 and, therefore, will not be repeated herein in the interest of brevity. The system 600 of FIG. 6 further includes an adapter 670 in accordance with some embodiments of the present invention. As discussed above, the adapter 670 is configured to allow a posterior imaging system to operate as an anterior imaging system. As illustrated in FIG. 6, in some embodiments of the present invention, the adapter 670 may include two lenses 673 and 675. The lenses 673 and 675 of the adapter 670 may have a focal length (F) of about 30.0 mm and a diameter (D) of about 25.4 mm. It will be understood that all the lenses 673 and 675 illustrated in FIG. 6 may be Achromat doublet lenses in accordance with some embodiments of the present invention. Furthermore, the arrangement of lenses provided in FIG. 6 are provided for exemplary purposes only and, therefore, embodiments of the present invention are not limited to the embodiments discussed herein.

As further illustrated in FIG. 6, the diverging ray bundles 609 including the collimated rays 607 from the object lens set 650/660 are incident on the adapter 670 including the two lenses 673 and 675. The adapter 670 acts as a single ideal lens to convert the diverging ray bundles to be parallel, and the collimated rays within each bundle to be focused on the object plane, thus providing for telecentric scanning of focused rays upon a flat object. This provides parallel ray bundles 611 including focusing rays 613 therein, the rays 613 being focused on the sample. The adapter 670 is designed for the case of a flat object. The lens system 670 may consist of a single lens with a focal length corresponding to the distance between the adapter position and the object position, or a combination of lenses having such focal length in combination. The lens combination may be chosen to minimize optical aberrations using lens design procedures, which are well known in the art. In particular, one combination of lenses which works well is a pair of achromatic doublet lenses each having nominal focal length equal to half the distance between the lens adapter and the sample, arranged in an opposing configuration as illustrated in FIG. 6.

Figure 7:
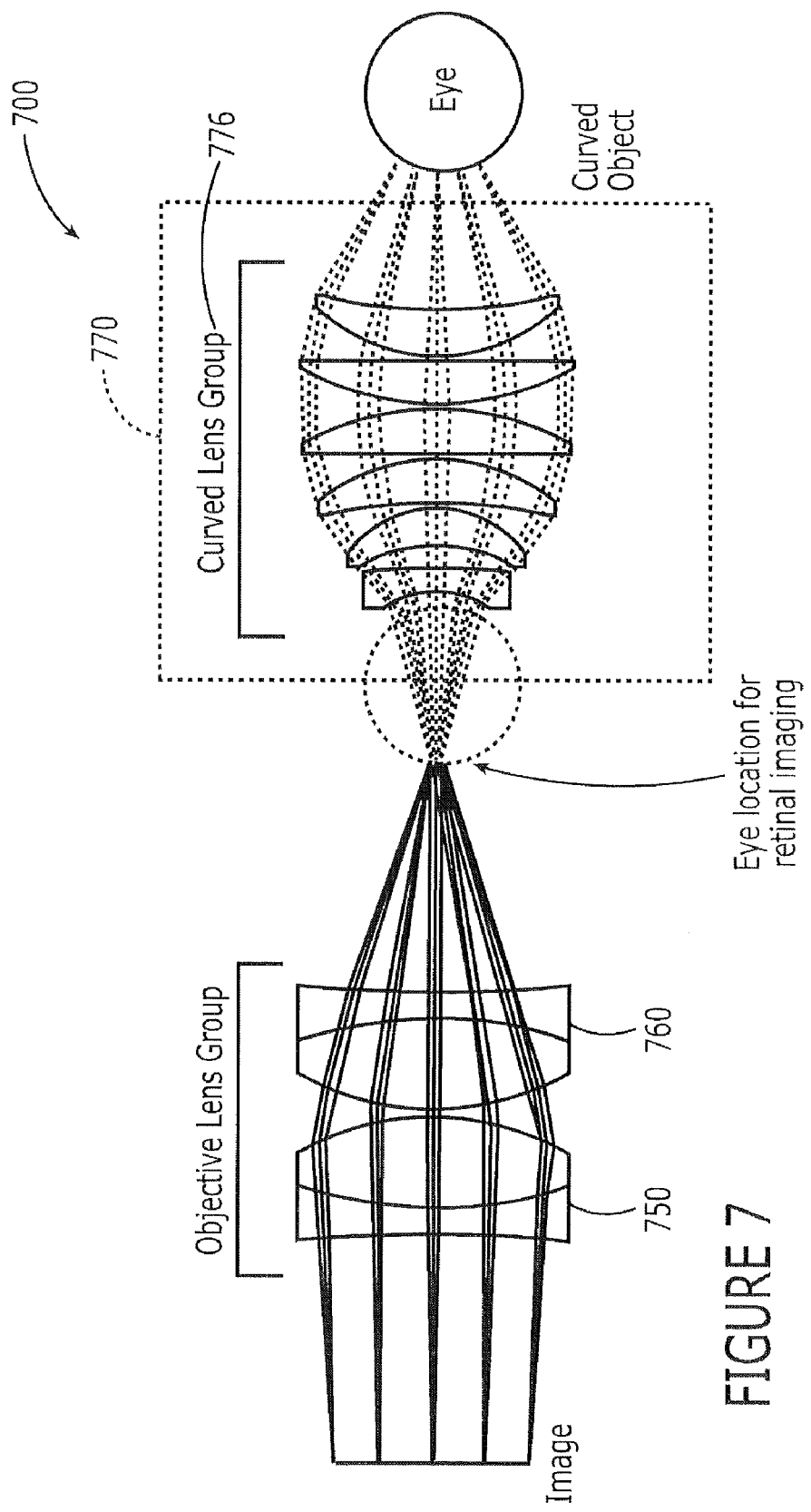
FIG. 7 illustrating a sample arm of an adaptable imaging system including a curved adapter according to some embodiments of the present invention.

Referring now to FIG. 7, an alternative lens set 776 for the adapter 770 will be discussed. Like reference numbers refer to like elements throughout the specification. Thus, the details with respect to the objective lens set 750/760 are similar to those discussed above with respect to FIG. 5 and, therefore, will not be repeated herein in the interest of brevity. As illustrated in FIG. 7, the adapter 770 includes a curved lens group 776. As will be discussed further herein, the curved lens set 776 may provide embodiments where the rays are more perpendicular to the surface of a curved sample. This may provide a stronger signal for layered structures, such as the cornea.

Furthermore, imaging depth is more limited in FDOCT systems than TDOCT systems, since in FDOCT systems there is be a fall off in sensitivity as the depth increases. In accordance with embodiments of the present invention illustrated in FIG. 7, converging optics may essentially flatten the structure being imaged and, therefore, provide more detailed images within the readily achievable depth range of FDOCT systems For example, the human eye does not have a uniform curvature. In particular, radius of curvature of portions of the eye may vary from about 8.0mm (for the cornea) to about 12.0mm (for the rest of the globe). The curved lens set 776 illustrated in FIG. 7 may provide a lens designed to form a flat image of a curved object, for example, the human eye. The rays are normal to the curved surface to allow a zero optical path difference across the entire field of view. The curved lens set 776 is configured to adapt to an existing retinal imager or OCT scanner to achieve cornea and OCT imaging in a flat plane. In other words, the curved lens set 776 or multi-element lens may be configured to image a curved object, such as the surface of the cornea, onto a flat plane, such as the intermediate focus plane behind the scanning and objective lenses As illustrated in FIG. 7, the curved lens group 776 may be adapted to such an imager. The objective lens set 750/760 of the retinal imager is configured to have the entrance aperture coincident with the pupil of the eye, similar to an eyepiece design. The image can then be relayed to, for example, a CCD camera for imaging or a scanning laser source for OCT. The curved lens set 776 in accordance with some embodiments of the present invention may use the same entrance aperture for the cornea image. Some embodiments of the present invention illustrated in FIG. 7, may provide substantially equal optical path lengths over the entire field, focus on a curved surface, and provide chief rays (the center ray of each ray bundle) normal to the curved surface, for example, the human eye.

It will be understood that "projecting a curved surface onto a flat plane" as discussed herein includes substantially projecting a curved surface onto a flat plane.

Some embodiments of the present invention provide optical systems for OCT that include scanning optics that provide for generating a scanning beam that pivots angularly about a point posterior to the cornea and placing the focal position in the posterior pole on the retina. In some embodiments of the present invention, an additional system of lens is provided that turns the pivoting scan geometry into a telecentric or near-telecentric scan geometry. In still further embodiments of the present invention an additional system of lenses is provided to that turns a system that is telecentric or near-telecentric with respect to a planar object into a system that is telecentric or near-telecentric with respect to a curved object. In some embodiments of the present invention, the additional system of lenses is provided that turns the pivoting scan geometry into a quasi-telecentric scan that provides a scanning beam nominally normal to the surface of the cornea. In some embodiments of the present invention, the additional system of lens provided moves the focal region from the posterior pole to the anterior chamber. In some embodiments of the present invention, the additional system of lens provided moves the focal region from the posterior pole to a depth compatible for imaging the cornea. In some embodiments of the present invention, the additional system of lenses provided moves the focal region from the posterior pole to a depth compatible for imaging the cornea. In some embodiments of the present invention, the lens system comprises a zoom lens configuration with a range of performance that encompasses some or all of the attributes desired in the invention. In some embodiments of the invention, the mechanical changes are accomplished through manual manipulation of the imaging system. In some embodiments of the invention, the mechanical changes are accomplished through software control.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A scanning optical imaging system configured to focus scanned rays of light onto a region of a subject to be imaged, the optical imaging system being adaptable for either of at least two scanning modes, the system comprising:
   first lens optics for use in a first mode, the first lens optics being adapted to converge the scanned rays to a pivot and to focus the scanned rays onto a first region of the subject to be imaged, the pivot being between the first lens optics and the first region along an optical path of the system; and
   second lens optics for use in a second mode, the second lens optics being adapted to focus the scanned rays onto a second region of the subject, different from the first region, without having converged the scanned rays to a pivot between the second lens optics and the second region.

2. The system of claim 1, wherein the second lens optics includes the first lens optics and at least one additional lens element.

3. The system of claim 1, wherein a portion of the second lens optics is coupled to the system such that removing the portion of the second lens optics from the optical path configures the system for operation in the first mode and positioning the portion of the second lens optics in the optical path configures the system for operation in the second mode.

4. The system of claim 1, wherein a portion of the first lens optics is coupled to the system such that removing the portion of the first lens optics from the optical path configures the system for operation in the second mode and positioning the portion of the first lens optics in the optical path configures the system for operation in the first mode.

5. The system of claim 1, wherein the second lens optics is coupled to the system such that removing the second lens optics from the optical path and replacing the second lens optics with the first lens optics configures the system for operation in the first mode, and wherein the first lens optics is coupled to the system such that removing the first lens optics from the optical path and replacing the first lens optics with the second lens optics configures the system for operation in the second mode.

6. The system of claim 1, wherein the scanning optical system is an Optical Coherence Tomography imaging system.

7. The system of claim 1, wherein the subject is an eye.

8. The system of claim 1, wherein the subject has an anterior structure and a posterior structure and an aperture separating at least a portion of the anterior structure from the posterior structure, the second region being in the anterior structure, and the first region being in the posterior structure.

9. The system of claim 1, wherein the second lens optics comprises a substantially telecentric optical lens assembly.

10. The system of claim 1, wherein the second lens optics comprises an optical lens assembly adapted to image a curved surface substantially onto a plane.

11. The system of claim 10, wherein the optical lens assembly comprises a multi-element curved lens group.

12. The system of claim 10 where the radius of curvature of the subject to be imaged to a plane is from about 8 mm to about 12 mm.

13. The system of claim 1:
   wherein the scanning optical system is an Optical Coherence Tomography imaging system;
   wherein the subject is an eye;
   wherein the first lens optics is adapted to image a posterior structure of the eye; and
   wherein the second lens optics is adapted to image an anterior structure of an eye.

14. The system of claim 13, wherein the anterior structure of the eye includes at least one of an anterior chamber, a cornea, a sclera, a conjunctiva, an iris, and a lens.

15. The system of claim 13, wherein the posterior structure of the eye includes at least one of a posterior pole and a retina.

16. A scanning optical imaging system adaptable for either of at least two operating modes, the system comprising:
   first lens optics for use in a first mode, the first lens optics being adapted for imaging a region of a subject posterior to an aperture of a subject; and
   second lens optics for use in a second mode, different from the first mode, the second lens optics being adapted for imaging a region of a subject anterior to or proximal to an aperture of the subject.

17. The system of claim 16, wherein the second lens optics includes the first lens optics and at least one additional lens element.

18. The system of claim 16, wherein a portion of the second lens optics is coupled to the system such that removing the portion of the second lens optics from an optical path of the system configures the system for operation in the first mode and positioning the portion of the second lens optics in the optical path configures the system for operation in the second mode.

19. The system of claim 16, wherein a portion of the first lens optics is coupled to the system such that removing the portion of the first lens optics from an optical path of the system configures the system for operation in the second mode and positioning the portion of the first lens optics in the optical path configures the system for operation in the first mode.

20. The system of claim 16, wherein the second lens optics is coupled to the system such that removing the second lens optics from the optical path and replacing the second lens optics with the first lens optics configures the system for operation in the first mode, and wherein the first lens optics is coupled to the system such that removing the first lens optics from the optical path and replacing the first lens optics with the second lens optics configures the system for operation in the second mode.

21. The system of claim 16, wherein the scanning optical system is an Optical Coherence Tomography imaging system.

22. The system of claim 16, wherein the subject is an eye.

23. The system of claim 16, wherein the eye has an anterior structure, and aperture, and a posterior structure.

24. The system of claim 23, wherein the anterior structure of the eye includes at least one of an anterior chamber, a cornea, a sclera, a conjunctiva, an iris, an anterior angle, and a lens.

25. The system of claim 23, wherein the posterior structure of the eye includes at least one of a posterior pole and a retina.

26. The system of claim 16, wherein the second lens optics comprises a substantially telecentric optical lens assembly.

27. The system of claim 16, wherein the second lens optics comprises an optical lens assembly that images a curved surface substantially onto a plane.

28. The system of claim 27, wherein the optical lens assembly comprises a multi-element curved lens group.

29. The system of claim 27, wherein the radius of curvature of the subject to be imaged substantially onto a plane is from about 8 mm to about 12 mm.

30. A converging scanning optical imaging system configured to focus a scanned ray of light onto a region of a subject to be imaged, the optical imaging system comprising an optical lens assembly that images a curved surface substantially onto a plane.

31. The system of claim 30, wherein the scanning optical system is an Optical Coherence Tomography imaging system.

32. The system of claim 30, wherein the subject is an anterior structure of an eye.

33. The system of claim 30, wherein the optical lens assembly comprises a multi-element curved lens group.

34. The system of claim 30, wherein the radius of curvature of the subject to be imaged substantially onto a plane is from about 8 mm to about 12 mm.

35. The system of claim 30, wherein the system is configured to image an anterior structure of the eye.

\* \* \* \* \*